United States Patent

Audia et al.

Patent Number: 5,886,004
Date of Patent: Mar. 23, 1999

[54] TETRAHYDROBETACARBOLINE COMPOUNDS

[75] Inventors: James E. Audia, Indianapolis; David L. G. Nelson, Carmel, both of Ind.

[73] Assignee: Eli Lilly and Company, Indianapolis, Ind.

[21] Appl. No.: 823,456

[22] Filed: Mar. 24, 1997

Related U.S. Application Data

[60] Provisional application No. 60/014,119, Mar. 25, 1996.

[51] Int. Cl.[6] .................. A61K 31/44; C07D 471/04; C07D 487/04
[52] U.S. Cl. ................... 514/280; 514/285; 514/292; 546/70; 546/85; 546/86; 546/276.7
[58] Field of Search ................... 546/86, 70, 85, 546/276.7; 514/280, 183, 285, 292

[56] References Cited

U.S. PATENT DOCUMENTS

| | | |
|---|---|---|
| 5,500,431 | 3/1996 | Audia et al. . |
| 5,643,916 | 7/1997 | Audia et al. ............. 514/285 |

FOREIGN PATENT DOCUMENTS

WO 95/24200   9/1995   WIPO ............. A61K 31/55

OTHER PUBLICATIONS

Kametani, Tetsuji, et al., "Studies on the Syntheses of Heterocyclic Compounds. DCXLI. A Convenient Synthesis of Hexadehydroyohimbine and a Total Synthesis of Yohimbine", Chem.Pharm.Bull., vol. 23, No. 11, pp. 2634–2642, (1975).

Hirai, Yoshiro, et al., "The Photochemistry of Keto–Imine Compounds", Heterocycles, vol. 21, No. 2, p. 725, (1984).

Kametani, Tetsuji, et al., "A Facile Synthesis of the Spirobenzylisoquinolines and the Spirobenzylcarbolines", Heterocycles, vol. 2, No.3, pp. 339–344, (1974).

Kursar, Jonathan, et al., "Molecular Cloning, Functional Expression, and Pharmacological Characterization of a Novel Serotonin Receptor (5–Hydroxytryptamine$_{2F}$) from Rat Stomach Fundus", Molecular Pharmacology, 42:549–557, (1992).

Wainscott, David B., et al., "Pharmacological Characteristics of the Newly Cloned Rat 5–Hydroxytryptamine$_{2F}$ Receptor", Molecular Pharmacology, 43:419–426, (1992).

Wainscott, David B., et al., "Pharmacologic Characterization of the Human 5–Hydroxytryptamine$_{2B}$ Receptor: Evidence for Species Differences", JPET, 276:720–727, (1996).

Kametani, et al., "Studies on the syntheses of heterocyclic compounds DCXLI. A convenient synthesis of hexadehydroyohimbine and a total synthesis of yohimbine.", Chem. Pharm. Bull. 23:11, pp. 2634–2642, (1975).

Primary Examiner—Mukund J. Shah
Assistant Examiner—Pavanaram K Sripada
Attorney, Agent, or Firm—Arleen Palmberg

[57] ABSTRACT

The present invention provides novel tetrahydro-beta-carboline compounds having useful central nervous system activity. The invention provides formulations and methods for using the novel tetrahydro-beta-carboline and related compounds. Such compounds are particularly useful for the modulation of a 5-HT$_{2B}$ receptor.

23 Claims, No Drawings

TETRAHYDROBETACARBOLINE COMPOUNDS

This application claims the benefit of U.S. Provisional Application No. 60/014,119, filed Mar. 25, 1996.

FIELD OF THE INVENTION

The present invention relates to the field of organic chemistry. The invention provides novel tetrahydro-beta-carboline compounds with exceptional selectivity and potency at a $5HT_{2B}$ receptor.

BACKGROUND OF THE INVENTION

Specific 5-HT receptor sites include $5\text{-}HT_{1A}$, $5\text{-}HT_{1B}$, $5\text{-}HT_{1D}$, $5\text{-}HT_{2A}$, $5\text{-}HT_{2B}$, $5\text{-}HT_{2C}$, $5\text{-}HT_3$, and $5\text{-}HT_4$ sites. Each of these receptors mediates certain physiological effects. See Leonard, B. E., *International Clinical Psychopharmacology*, 7:13–21 (1992). It is particularly desired to obtain compounds which selectively mediate certain of the 5-HT receptor sites. The present invention provides new compounds which are particularly useful for modulating a $5\text{-}HT_{2B}$ receptor with surprising selectivity and potency.

SUMMARY OF THE INVENTION

This invention provides a group of novel compounds with $5\text{-}HT_{2B}$ receptor activity. Additionally, the present compounds are useful tools to characterize the effects of the $5\text{-}HT_{2B}$ receptor and to develop therapeutic agents based on $5\text{-}HT_{2B}$ receptor modulation.

The present invention provides compounds of the Formula I

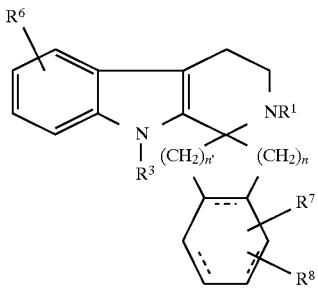

wherein
$R^1$ is hydrogen or $C_1$–$C_3$ alkyl;
$R^3$ is hydrogen or $C_1$–$C_3$ alkyl;
$R^6$ is selected from the group consisting of hydrogen, $C_1$–$C_6$ alkyl, $C_2$–$C_6$ alkenyl, halo, halo ($C_1$–$C_6$) alkyl, halo ($C_2$–$C_6$) alkenyl, $COR_5$, $C_1$–$C_{10}$ alkanoyl, $CO_2R_5'$, $(C_1$–$C_6$ alkyl$)_m$ amino, $NO_2$, —$SR_5$, and $OR_5$;
$R^7$ and $R^8$ are independently selected from the group consisting of hydrogen, $C_1$–$C_6$ alkyl, $C_2$–$C_6$ alkenyl, $NO_2$, halo, halo ($C_1$–$C_6$) alkyl, halo ($C_2$–$C_6$) alkenyl, $COR_5$, $C_1$–$C_{10}$ alkanoyl, $C_7$–$C_{16}$ arylalkyl, $CO_2R_5'$, $(C_1$–$C_6$ alkyl$)_m$ amino, —$SR_5$, and $OR_5$;
n is 1, 2, or 3;
n' is 1, 2, or 3;
m is 1 or 2;
$R_5$ is independently hydrogen or $C_1$–$C_4$ alkyl;
$R_5'$ is $C_1$–$C_4$ alkyl;
--- is optionally a bond;
a pharmaceutically acceptable salt or solvate thereof.

DETAILED DESCRIPTION OF THE INVENTION

The term "treating" as used herein includes prophylaxis of the named physical and/or mental condition or amelioration or elimination of the developed physical and/or mental condition once it has been established.

The terms "$C_1$–$C_n$ alkyl" wherein n=2–10, as used herein, represent a branched or linear alkyl group having from one to the specified number of carbon atoms. Typical $C_1$–$C_6$ alkyl groups include methyl, ethyl, n-propyl, iso-propyl, butyl, iso-butyl, sec-butyl, tert-butyl, pentyl, hexyl and the like.

The terms "$C_2$–$C_n$ alkenyl" wherein n=3–10, as used herein, represents an olefinically unsaturated branched or linear group having from 2 to 10 carbon atoms and at least one double bond. The groups can be branched or straight chain. Examples of such groups include 1-propenyl, 2-propenyl (—$CH_2$—$CH$=$CH_2$), 1,3-butadienyl (—$CH$=$CHCH$=$CH_2$), 1-butenyl (—$CH$=$CHCH_2CH_3$), hexenyl, pentenyl, and the like.

The terms "halide", "halogen", and "halo" include fluorine, chlorine, bromine, and iodine. The preferred halogen is chlorine.

The terms "halo($C_1$–$C_6$)alkyl" and "halo($C_2$–$C_6$) alkenyl" refer to alkyl or alkenyl substituents having one or more independently selected halo atoms attached at one or more available carbon atoms. These terms include chloromethyl, bromoethyl, trifluoroethyl, trifluoromethyl, trifluoroethylenyl, 3-bromopropyl, 3-bromo-1-propenyl, 2-bromopropyl, 2-bromo-1-propenyl, 3-chlorobutyl, 3-chloro-2-butenyl, 2,3-dichlorobutyl, chloroethylenyl, 5-fluoro-3-pentenyl, 3-chloro-2-bromo-5-hexenyl, 3-chloro-2-bromobutyl, trichloromethyl, dichloroethyl, 1,4-dichlorobutyl, 3-bromopentyl, 1,3-dichlorobutyl, 1,1-dichloropropyl, and the like. More preferred halo-($C_1$–$C_6$) alkyl groups are trichloromethyl, trichloroethyl, and trifluoromethyl. The most preferred halo-($C_1$–$C_6$)alkyl is trifluoromethyl.

The term "$C_1$–$C_{10}$ alkanoyl" represents a group of the formula $C(O)$ ($C_1$–$C_9$) alkyl. Typical $C_1$–$C_{10}$ alkanoyl groups include acetyl, propanoyl, butanoyl, and the like.

The term "($C_1$–$C_6$ alkyl$)_m$ amino" wherein m=1–2; refers to either a mono- or a dialkylamino group in which the alkyl portion of the group may be straight or branched. Examples of such groups are methylamino, dimethylamino, ethylamino, diethylamino, 2-propylamino, 1-propylamino, di(n-propyl)amino, di(iso-propyl)amino, methyl-n-propylamino, t-butylamino, and the like.

The term "$C_3$–$C_n$ cycloalkyl" wherein n=4–8, represents cyclopropyl, cyclobutyl, cyclopentyl, cyclohexyl, cycloheptyl, and cyclooctyl.

The term "substituted($C_5$–$C_n$) cycloalkyl" refers to a cycloalkyl group as described supra wherein the cycloalkyl group may be substituted with from one to four substituents independently selected from the group consisting of hydrogen, $C_1$–$C_6$ alkyl, $NO_2$, halo, halo($C_2$–$C_6$)alkyl, halo ($C_2$–$C_6$) alkenyl, $C_2$–$C_6$ alkenyl, $CO_2R_5$, ($C_1$–$C_6$ alkyl$)_m$ amino, —$SR_5$, and $OR_5$.

The term "$C_3$–$C_8$ cycloalkyl-($C_1$–$C_3$)alkyl" represents a linear alkyl group substituted at a terminal carbon with a $C_3$–$C_8$ cycloalkyl group. Typical cycloalkylalkyl groups include cyclohexylethyl, cyclohexylmethyl, 3-cyclopentylpropyl, and the like.

The term "$C_5$–$C_8$ cycloalkenyl" represents an olefinically unsaturated ring having five to eight carbon atoms, eg., phenyl, cyclohexadienyl, cyclohexenyl, cyclopentenyl, cycloheptenyl, cyclooctenyl, cyclohexadienyl, cycloheptadienyl, cyclooctatrienyl and the like.

The term "substituted ($C_5$–$C_8$) cycloalkenyl" refers to a cycloalkenyl group as described supra wherein the cycloalkenyl group may be substituted with from one to four substituents independently selected from the group consisting of hydrogen, $C_1$–$C_6$ alkyl, $NO_2$, halo, halo($C_1$–$C_6$)alkyl, halo($C_2$–$C_6$)alkenyl, $C_2$–$C_6$ alkenyl, $COR_5$, $C_1$–$C_{10}$ alkanoyl, $C_7$–$C_{16}$ arylalkyl, $CO_2R_5$, ($C_1$–$C_6$ alkyl)$_m$ amino, —$SR_5$, and $OR_5$.

The term "$C_5$–$C_8$ cycloalkenyl-($C_1$–$C_3$)alkyl" represents a linear $C_1$–$C_3$ alkyl group substituted at a terminal carbon with a $C_5$–$C_8$ cycloalkenyl group.

The term "aryl" represents phenyl or naphthyl. The aryl group can be unsubstituted or can have one or two substituents independently selected from the group consisting of $C_1$–$C_6$ alkyl, $C_3$–$C_8$ cycloalkyl, substituted $C_3$–$C_8$ cycloalkyl, $C_2$–$C_6$ alkenyl, $C_3$–$C_8$ cycloalkyl-($C_1$–$C_3$)alkyl, phenyl, $C_5$–$C_8$ cycloalkenyl, substituted $C_5$–$C_8$ cycloalkenyl, $C_5$–$C_8$ cycloalkenyl-($C_1$–$C_3$)alkyl, $COR_5$, $C_1$–$C_{10}$ alkanoyl, $OR_5$, and $C_7$–$C_{16}$ arylalkyl. The substituents may be located at any available position on the aryl ring.

The term "$C_7$–$C_{16}$ arylalkyl" represents an aryl-($C_1$–$C_{10}$) alkyl substituent wherein the alkyl group is linear, such as benzyl, phenethyl, 3-phenylpropyl, or phenyl-t-butyl; or branched. The alkyl portion bonds at the point of attachment to the parent molecule.

The term "selective binding of a 5-$HT_{2B}$ receptor" refers to a method of binding the 5-$HT_{2B}$ receptor to a greater extent than it binds a 5-$HT_{2A}$ and/or 5-$HT_{2C}$ receptors.

The term "protic acid" refers to an acid having an acidic hydrogen. Preferred protic acids include hydrochloric acid, formic acid, perchloric acid, sulfuric acid, and phosphoric acid in an aqueous medium. The most preferred protic acids are hydrochloric acid, sulfuric acid, and formic acid.

The term "organic solvent" includes solvents containing carbon, such as halogenated hydrocarbons, ether, toluene, xylene, benzene, and tetrahydrofuran.

The term "agitate" includes such techniques as stirring, centrifugation, mixing, and other similar methods.

The term "aprotic solvent" refers to polar solvents of moderately high dielectric constant which do not contain an acidic hydrogen. Examples of common aprotic solvents are dimethyl sulfoxide (DMSO), dimethylformamide, sulfolane, tetrahydrofuran, diethyl ether, methyl-t-butyl ether, or 1,2-dimethoxyethane.

The term "protic solvent" refers to a solvent containing hydrogen that is attached to oxygen, and hence is appreciably acidic. Common protic solvents include such solvents as water, methanol, ethanol, 2-propanol, and 1-butanol.

The term "inert atmosphere" refers to reaction conditions in which the mixture is covered with a layer of inert gas such as nitrogen or argon.

Abbreviations used herein have their accepted meaning, unless stated otherwise. For example, "Me" and "Et" refer to methyl, ethyl respectively, and "t-Bu" refers to tertiary-butyl. The abbreviation "RT" refers to room temperature or ambient conditions unless indicated otherwise.

The term "ligand" refers to compounds that are bound by the 5-$HT_{2B}$ receptor. Compounds useful as 5-$HT_{2B}$ selective ligands may be used to selectively occupy a 5-$HT_{2B}$ receptor site or may act as a selective agonist at a 5-$HT_{2B}$ receptor site.

The term "substantially pure" is intended to mean at least about 90 mole percent, more preferably at least about 95 mole percent, and most preferably at least about 98 mole percent of the desired enantiomer or stereoisomer is present compared to other possible configurations.

As used herein the term "functional bowel disorder" refers to a functional gastrointestinal disorder manifested by (1) abdominal pain and/or (2) symptoms of disturbed defecation (urgency, straining, feeling of incomplete evacuation, altered stool form [consistency] and altered bowel frequency/timing) and/or (3) bloating (distention). The term "functional bowel disorder" includes but is not limited to irritable bowel syndrome, hypermotility, ichlasia, hypertonic lower esophogeal sphincter, tachygastria, constipation, hypermotility associated with irritable bowel syndrome.

It has been discovered the 5-$HT_{2B}$ receptor is localized in the rat lung, stomach fundus, uterus, bladder, and colon. Interesting areas of 5-$HT_{2B}$ receptor localization in the human include but are not limited to the brain and blood vessels. Thus, conditions which can be treated using a compound which modulates a 5-$HT_{2B}$ receptor includes, for example, psychosis, depression, anxiety disorders, uterine diseases such as endometriosis, fibrosis, and other abnormal uterine contractivity, panic attack, migraine, eating disorders, seasonal affective disorder, consumption disorders, cardiovascular conditions, such as thrombosis, hypertension, angina, vasospasm, and other vascular occlusive diseases, incontinence, bladder dysfunction, respiratory/airway disorders including asthma, functional bowel disorders and the like.

The formula (I) compounds claimed herein can form acid addition salts with a wide variety of inorganic and organic acids. Typical acids which can be used include sulfuric, hydrochloric, hydrobromic, phosphoric, hypophosphoric, hydroiodic, sulfamic, citric, acetic, maleic, malic, succinic, tartaric, cinnamic, benzoic, ascorbic, mandelic, p-toluenesulfonic, benzenesulfonic, methanesulfonic, trifluoroacetic, hippuric and the like. The pharmaceutically acceptable acid addition salts of the Formula (I) compounds are especially preferred.

As used herein, in particular with respect to the preferred embodiments set forth in tabular form below, the following numbering system shall apply:

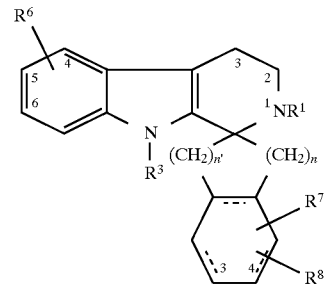

The compounds of the present invention are useful for modulating or blocking the 5-$HT_{2B}$ receptor. Certain of the present compounds are preferred for that use. The following invention embodiments and compound characteristics listed in tabular form may be independently selected or combined to produce a variety of preferred compounds and embodiments of the invention. The following list of embodiments of this invention is in no way intended to limit the scope of this invention in any way.

A) $R^1$ is hydrogen;

B) the spiro group is a naphthyl analog;

C) $R^3$ is hydrogen or methyl;

D) $R^3$ is hydrogen;

E) n is 1 and n' is 2;

F) --- are double bonds to provide an aromatic ring;

G) n is 1 and n' is 1;

H) n is 1 or 2 and n' is 1;

I) $R^6$ is located at the 5-position of the phenyl ring;

J) $R^6$ is hydrogen, methyl, chloro, or bromo;

K) n is 3 and n' is 2;

L) $R^6$ is hydrogen, methyl, chloro, or bromo; $R_7$ and $R_8$ are independently selected from the group consisting of methoxy and ethoxy;

M) $R^7$ and $R^8$ are independently selected from the group consisting of halo and $C_1$–$C_4$ alkyl;

N) $R^7$ and $R^8$ are at the 3 and 4 positions;

O) $R^7$ and $R^8$ are each methoxy or ethoxy;

P) A compound having preferred characteristics described supra;

Q) A method for selectively binding a $5HT_{2B}$ receptor using one or more compounds of Formula I;

R) A method for binding a $5HT_{2B}$ receptor using one or more compounds of Formula I;

S) A method of using one or more compounds of Formula I for treating a functional bowel disorder;

T) A pharmaceutical formulation comprising a compound of Formula I and one or more pharmaceutically acceptable excipients.

U) A particularly preferred embodiment is the compound of Example 1, herein.

Examples of compounds of Formula I include but are not limited to:
spiro-9,9[2-(3,4-dichloro)-1,2,3,4-tetrahydronaphthyl]-5-methoxy-1,2,3,9-tetrahydro-8H-pyrido indole, spiro-9,9[2-(3,4-dimethoxy)-1,2,3,4-tetrahydronaphthyl]-5-methyl-1,2,3,9-tetrahydro-8H-pyrido indole, spiro-9,9[2-(3,4-diethoxy)-1,2,3,4-tetrahydronaphthyl]-5-methyl-1,2,3,9-tetrahydro-8H-pyrido indole, spiro-9,9[2-(3,5-dichloro)-1,2,3,4-tetrahydronaphthyl]-5-dimethylamino-1,2,3,9-tetrahydro-8H-pyrido indole, spiro-9,9[2-(3-fluoro,4-chloro)-1,2,3,4-tetrahydronaphthyl]-5-ethyl-1,2,3,9-tetrahydro-8H-pyrido indole, spiro-9,9[2-(3,4-dimethoxy)-1,2,3,4-tetrahydronaphthyl]-5-chloro-1,2,3,9-tetrahydro-8H-pyrido indole, spiro-9,9[2-(3,4-dimethoxy)-1,2,3,4-tetrahydronaphthyl]-5-bromo-1,2,3,9-tetrahydro-8H-pyrido indole, spiro-9,9[2-(3,4-dimethoxy)-1,2,3,4-tetrahydronaphthyl]-5-chloro-1,2,3,9-tetrahydro-8H-pyrido indole.

The present invention contemplates racemic mixtures as well as the substantially pure stereoisomers of the compounds of Formulas I. The term "enantiomer" is used herein as commonly used in organic chemistry to denote a compound which rotates the plane of polarization. Thus, the "–enantiomer" rotates the plane of polarized light to the left, and contemplates the levorotary compound of Formula I. The + and – enantiomers can be isolated using well-known classical resolution techniques. One particularly useful reference which describes such methods is JACQUES et. al. ENANTIOMERS, RACEMATES, AND RESOLUTIONS (John Wiley and Sons 1981). Appropriate resolution methods include direct crystallization, entrainment, and crystallization by optically active solvents. Chrisey, L. A. *Heterocycles*, 267:30 (1990). Preferred optically active acids include camphorsulfonic and derivatives of tartaric acid.

The present invention encompasses both the R and the S configurations. The terms "R" and "S" are used herein as commonly used in organic chemistry to denote the specific configuration of a chiral center. See, R. T. Morrison and R. N. Boyd, *Organic Chemistry*, pp 138–139 (4th Ed. Allyn & Bacon, Inc., Boston) and Orchin, et al. *The Vocabulary of Organic Chemistry*, p. 126, (John Wiley and Sons, Inc.). Thus the present invention encompasses both the cis and trans conformation of each particular compound.

The compounds of the present invention are known to form hydrates and solvates with appropriate solvents. Preferred solvents for the preparation of solvate forms include water, alcohols, tetrahydrofuran, DMF, and DMSO. Preferred alcohols are methanol and ethanol. Other appropriate solvents may be selected based on the size of the solvent molecule. Small solvent molecules are preferred to facilitate the corresponding solvate formation. The solvate or hydrate is typically formed in the course of recrystallization or in the course of salt formation. One useful reference concerning solvates is Sykes, Peter, A *Guidebook to Mechanism in Organic Chemistry*, 6:56 (1986, John Wiley & Sons, New York). The term "solvate" as used herein includes hydrate forms such as monohydrate and dihydrates.

The compounds of the present invention can be prepared using chemical processes that are understood in the art; however, a most preferred method for preparing the compounds of Formulas I is illustrated by Scheme I

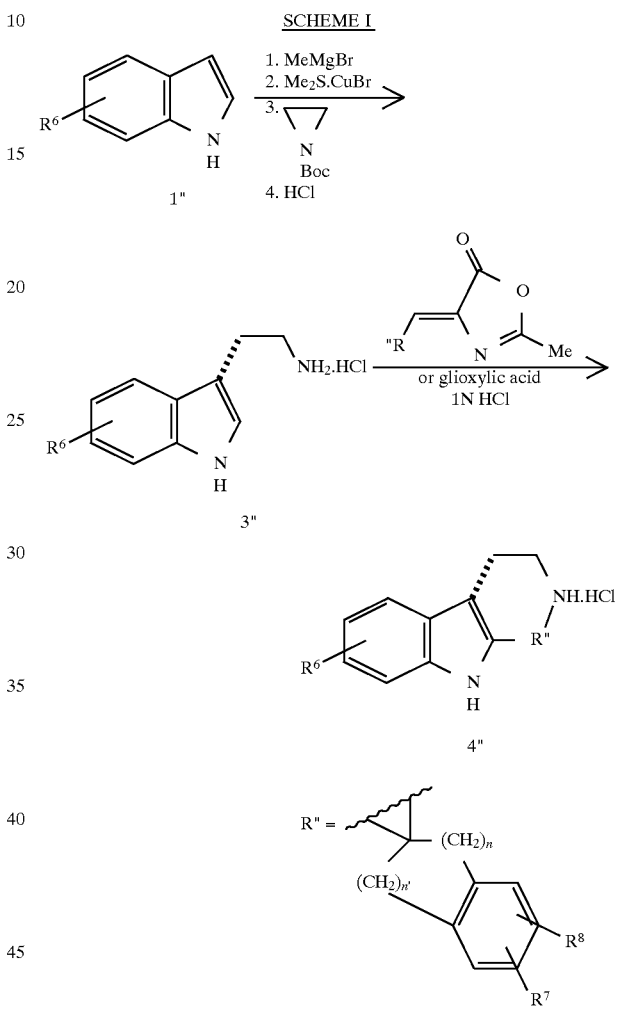

As illustrated in Scheme I, the n, n', $R^6$, $R^7$, and $R^8$ substituents are as defined supra.

The following Examples further illustrate the preparation of certain of the Formula I compounds. The examples are illustrative only, and are not intended to limit the scope of the invention.

The column chromatography procedures used standard flash chromotagraphy techniques. One well-known reference describing appropriate flash chromotagraphy techniques is Still, W. C. Kahn, and Mitra, *J. Org. Chem.*, 43, 2932, (1978). Fractions containing product were generally evaporated under reduced vacuum to provide the product.

Optical rotations were obtained using methanol, pyridine, or other suitable solvent.

The hydrochloride salt of the particular compound was prepared by placing the free base into diethyl ether containing an alcohol such as methanol or other suitable solvent mixture. While stirring this ether solution, a solution of HCl in diethyl ether was added dropwise until the solution became acidic. Alternatively, the ether solution was treated with dry HCl gas.

The maleate salt of the particular compound was prepared by placing the free base in ethyl acetate or other suitable solvent and treating with maleic acid. The precipitate formed was filtered and dried to provide the corresponding hydrochloride or maleate salt of the free base.

For the following Examples, where applicable, diethylether was distilled from sodium benzophenone ketyl prior to use. All reactions were performed under a positive pressure of argon. $^1$H-NMR and $^{13}$C-NMR data were recorded on a Bruker AC-200P (200 MHz). IR spectra were obtained on Nicolet 510 P-FT (film and KBr). Melting points were determined on a Büchi apparatus and are not corrected. Analytical TLC was performed on Merck TLC glass plates precoated with $F_{254}$ silica gel 60 (UV, 254 nm and Iodine). Chromatographic separations were performed by using 230–400 mesh silica gel (Merck). N-BOC-aziridines (2a–d) were prepared from the corresponding alkenes following standard procedures.

Preparation 1

Indole Starting Materials

The indole starting materials (1a, 1b, and 1c) infra. were purchased (1a), prepared according to Bartoli's procedure (1b) [Bartoli, G. et al. *Tetrahedron Lett.*, 1989, 30, 2129] or (1c) synthesized from 2-Iodo-4,6-dimethylaniline (5'''). The process is illustrated by the following SchemeIV:

Scheme IV

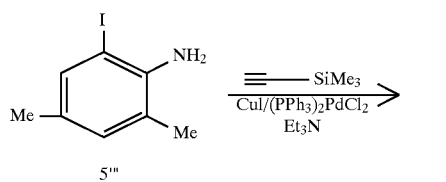

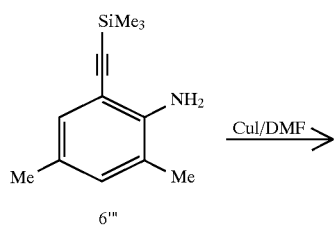

The 2-Iodo-4,6-dimethylaniline (5''') synthesis can be completed as follows: To a suspension of 5''' (24 mmol.), CuI (0.05 equiv.) and (PPh$_3$)$_2$PdCl$_2$ (0.05 equiv.) in 30 ml of dry triethylamine under Ar. atmosphere was added trimethylsilylacetylene (1.1 equiv.) and the resulting mixture was stirred for 3 hours. Then, the solvent was eliminated under vacuum and the residue purified by flash chromatography using hexane/ethyl acetate (3:1) as eluent to yield 6'' in quantitative yield. A slurry of 6''' (23 mmol.) and CuI (2 equiv.) in 50 ml of dry dimethyl formamide was heated for 2.5 h. under Ar. atmosphere at 100° C. After cooling down to room temperature the reaction mixture was filtered off and the solid washed twice with ether (20 ml.). The organic phase was washed with water (3×50 ml.), dried over Na$_2$SO$_4$ and the solvent evaporated to dryness. The crude product was purified by flash chromatography using hexane/ethyl acetate (3:1) as eluent to afford 1c (1.5 g., 45%).

EXAMPLE 1

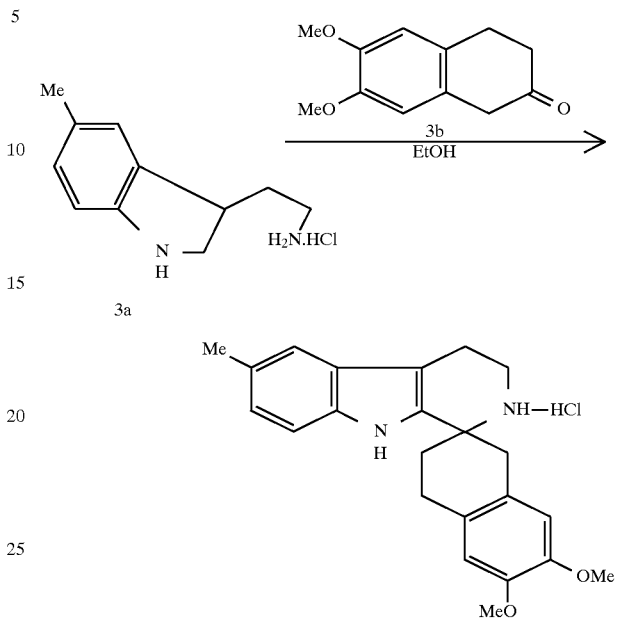

A suspension of the corresponding tryptamine hydrochloride (3a) (1 gram) and the correponding dimethoxytetralone (3b) (1 gram) in ethanol (10 ml.) was refluxed during 128 h. After this time the reaction mixture was allowed to reach room temperature and filtered off. The crude solid was washed and dried. Melting point 261° C.

|   | Theory | Found |
|---|--------|-------|
| C | 69.25  | 69.34 |
| H | 6.82   | 6.97  |
| N | 7.02   | 6.98  |

EXAMPKE 2

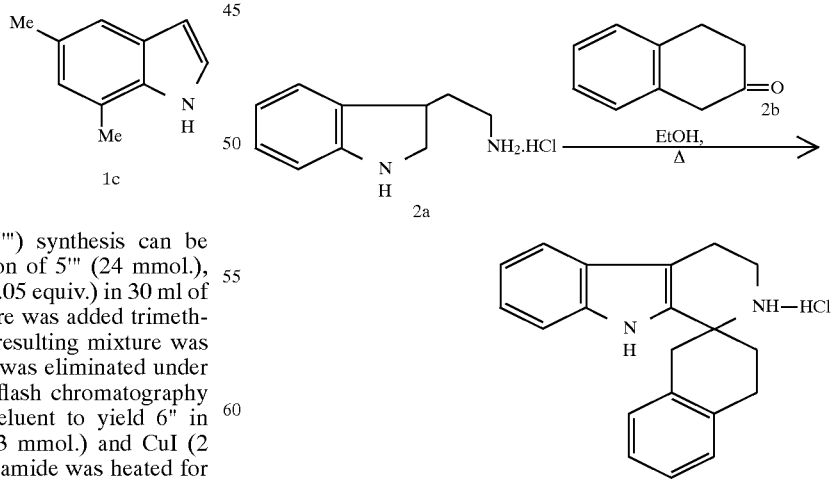

A suspension of the corresponding tryptamine hydrochloride (2a) (575 mg) and the correponding ketone (2b) (464 mg) in ethanol (10 ml.) was refluxed during 128 h. After this time the reaction mixture was allowed to reach room temperature and filtered off. The crude solid was washed and dried.

Yield: 525 mg

|   | Theory | Found |
|---|--------|-------|
| C | 74.43  | 74.36 |
| H | 6.84   | 6.84  |
| N | 8.27   | 8.25  |

MS: 301

EXAMPLE 3

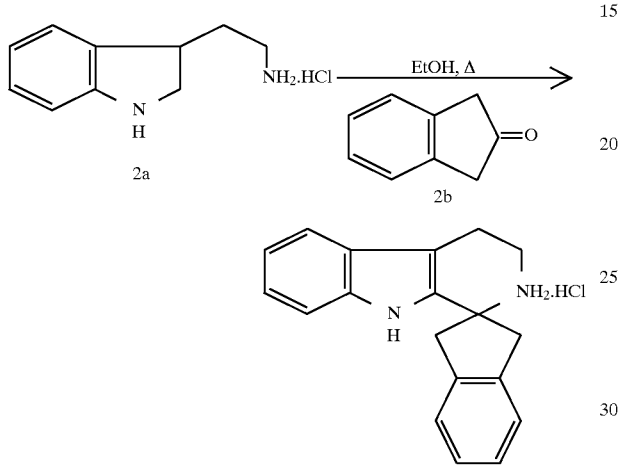

A suspension of the corresponding tryptamine hydrochloride (2a) (500 mg) and the correponding ketone (2b) (396 mg) in ethanol (10 ml.) was refluxed during 72 h. After this time the reaction mixture was cooled to about 0° C. and filtered off. The crude solid was washed and dried.

Yield: 262 mg
MS: 274

EXAMPLE 4

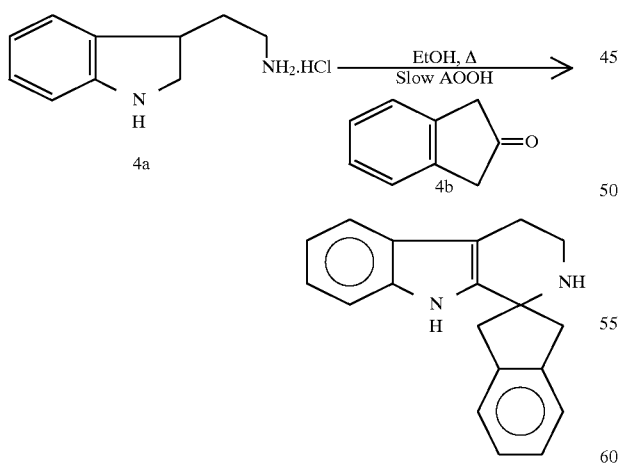

A suspension of the corresponding tryptamine hydrochloride (4a) (500 mg) and the correponding ketone (4b) (396 mg) in ethanol (10 ml.) was refluxed during 72 h. After this time the reaction mixture was cooled to about 0° C. for about 24 hours and filtered off. The crude solid was washed and dried.

Submitted for mass spectral analysis and found mi of 274.

EXAMPLE 5

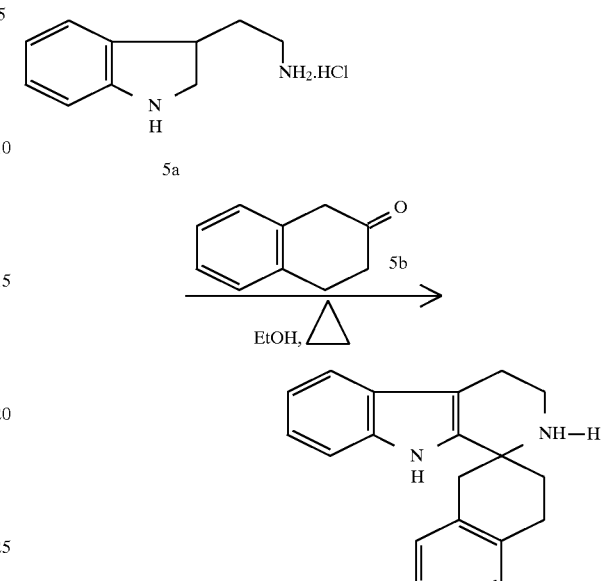

A suspension of the corresponding tryptamine hydrochloride (5a) (500 mg) and the correponding ketone (5b) (397 uL) in ethanol (10 ml.) was refluxed during 72 h. After this time the reaction mixture was cooled to about 0° C. for 14 hours and filtered off. The crude solid was washed and dried.

Yield: 630 mg

|   | Theory | Found |
|---|--------|-------|
| C | 73.95  | 73.32 |
| H | 6.52   | 6.73  |
| N | 8.62   | 8.59  |

MS: 288

EXAMPLE 6

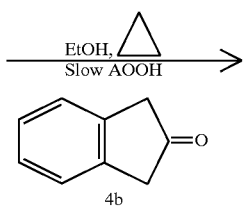

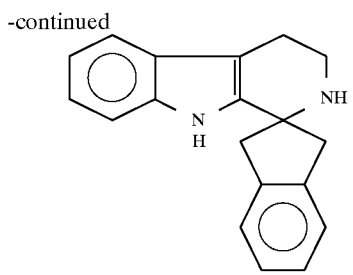

A suspension of the corresponding tryptamine hydrochloride (4a) (1 g) and the correponding ketone (4b) (800 mg) in ethanol (10 ml.) was refluxed during 72 h. After this time the reaction mixture was cooled to about 0° C. for about 24 hours and filtered off. The crude solid was washed and dried.

Yield: 550 mg

|   | Theory | Found |
|---|--------|-------|
| C | 70.67  | 70.88 |
| H | 7.06   | 7.16  |
| N | 7.85   | 7.88  |

As noted above, the compounds of the present invention are useful in blocking the effect of serotonin or other agonists at 5-$HT_{2B}$ receptors. Thus, the present invention also provides a method for blocking a 5-$HT_{2B}$ receptor in mammals comprising administering to a mammal requiring blocking of a 5-$HT_{2B}$ receptor a receptor blocking dose of a compound of the invention.

The term "receptor blocking dose", means an amount of compound necessary to block a targeted receptor in a mammal. The active compounds are effective over a wide dosage range. For example, dosages per day will normally fall within the range of about 0.05 to about 250 mg/kg of body weight. In the treatment of adult humans, the range of about 0.5 to 100 mg/kg, in single or divided doses, is preferred. The ranges of about 5 mg/kg to about 60 mg/kg and about 10 mg/kg to about 50 mg/kg are especially preferred. However, it will be understood that the amount of the compound actually administered will be determined by a physician in light of the relevant circumstances, including the condition to be treated, the choice of compound to be administered, the age, weight, and response of the individual patient, the severity of the patient's symptoms, and the chosen route of administration, and therefore the above dosage ranges are not intended to limit the scope of the invention in any way. The compounds may be administered by a variety of routes such as oral, transdermal, subcutaneous, intranasal, intramuscular, and intravenous routes.

One particularly useful embodiment of this invention is that it provides selective ligands for the 5-$HT_{2B}$ receptor. Compounds with a high affinity for the 5-$HT_{2B}$ receptor generally are cross-reactive with the 5-$HT_{2C}$ receptor as well. Now 5-$HT_{2B}$ receptors can be selectively modulated using compounds of this invention at rates set forth above for blocking the effects of agonists at 5-$HT_{2B}$ receptors. The selective affinity may provide treatments with fewer side effects and will facilitate the development of additional therapeutic agents.

Assay Procedure.

Radioligand binding assays for 5-$HT_{2B}$ receptors were conducted according to described methods. Kursar, Jonathan, et. al. *MOLECULAR PHARMACOLOGY*, 42:549–557 (1992), Wainscott, David et. al. *MOLECULAR PHARMACOLOGY*, 43:419–426 (1992), Wainscott, David et. al. *THE AMERICAN SOCIETY FOR PHARMACOLOGY AND EXPERIMENTAL THERAPEUTICS*, 276:720–727 (1996).

Certain compounds and intermediates of the present invention are useful for modulating 5-$HT_{2B}$ receptors. The compounds which are most useful for binding a 5$HT_{2B}$ receptor can be identified using the following procedures. Further, a useful in vivo model for demonstrating 5-$HT_{2B}$ activity is provided infra.

Radioligand Binding Studies for the 5-$HT_{2B}$ receptor:

Membrane preparation from transformed cells. Suspension cells expressing the cloned rat 5-$HT_{2B}$ receptor were harvested by centrifugation at 2,200×g for 15 min at 4° C. Kursar, J. D., D. L. Nelson, D. B. Wainscott, M. L. Cohen, and M. Baez, *Mol. Pharmacol.*, 42: 549–557 (1992). Membranes for the binding assays were prepared by vortexing the pellet in 50 mM Tris-HCl, pH 7.4 ($0.5 \times 10^9$ cells/30 ml). The tissue suspension was then centrifuged at 39,800×g for 10 min at 4° C. This procedure was repeated for a total of three washes, with a 10 minute incubation at 37° C. between the first and second wash. The final pellet was homogenized in 67 mM Tris-HCl, pH 7.4 (at 20–40 and 12.5 million cells/ml, original cell number, for cells expressing low and relatively high levels of the 5-$HT_{2B}$ receptor, respectively) using a Tissumizer (Tekmar, Cincinnati, Ohio.), setting 65 for 15 seconds.

[$^3$H]5-HT binding studies. Binding assays were automated using a Biomek 1000 (Beckman Instruments, Fullerton, Calif.) and were performed in triplicate in 0.8 ml total volume. Membrane suspension, 200 μl, (0.04–0.27 mg protein) and 200 μl of drug dilution in water were added to 400 μl of 67 mM Tris-HCl, pH 7.4, containing [$^3$H]5-HT, pargyline, $CaCl_2$, and L-ascorbic acid. Final concentrations of pargyline, $CaCl_2$ and L-ascorbic acid were 10 μM, 3 mM and 0.1%, respectively. Tubes were incubated at 37° C. for 15 min or at 0° C. for 2 hours (binding equilibria were verified for both of these conditions), then rapidly filtered using a Brandel cell harvester (Model MB-48R; Brandel, Gaithersburg, Md.) through Whatman GF/B filters which had been presoaked in 0.5% polyethylenimine and precooled with ice-cold 50 mM Tris-HCl, pH 7.4. The filters were then washed rapidly four times with one ml ice-cold 50 mM Tris-HCl, pH 7.4. The amount of [$^3$H]5-HT trapped on the filters was determined by liquid scintillation spectrometry (Ready Protein and Beckman LS 6000IC, Beckman Instruments, Fullerton, Calif.). For the saturation experiments, actual free radioligand concentrations were determined by sampling the supernatant of parallel saturation experiments in which bound radioactivity had been separated by centrifugation. The concentration of [$^3$H]5-HT ranged from 0.02 to 5 nM and 0.6 to 63 nM for saturation experiments incubated at 0° C. and 37° C., respectively. 5-HT, 10 μM, or 1-naphthylpiperazine (1-NP), 10 μM, defined nonspecific binding. For competition experiments, six to twelve concentrations of displacing drugs were used, spanning six log units, and the final concentration of [$^3$H] 5-HT was 2 nM. Protein was determined by the method of Bradford, using bovine serum albumin as the standard. Bradford, M. M., *Anal. Biochem.* 72: 248–254 (1976).

[$^3$H]Rauwolscine Binding Studies.

In addition to measuring the 5-$HT_{2B}$ receptor with the agonist [$^3$H]5-HT, the antagonist [$^3$H]Rauwolscine was also used (Nelson, D. L., et.al. *Soc. Neurosci. Abstr.* 21, Part 2:1124 (1995). Membranes from AV-12 cells (ATCC No. CRL 1573) stably transfected with the human 5-$HT_{2B}$ receptor were prepared as described above. Binding assays were performed in triplicate in 0.8 ml total volume. Membrane suspension, 200 μl, and 200 μl of drug dilution in water were added to 400 μl of 67 mM Tris-HCl, pH 7.4, with efaroxan to mask alpha-adrenergic receptors. Final concentrations of efaroxan of Tris were 500 nM and 50 mM, respectively.

Tubes were incubated at 37° C. for 20 minutes (equilibrium was verified for these conditions), then rapidly filtered through Watman GF/B filters (presoaked in 0.5% polyethyleneimine). The filters were then washed 4 times with one ml ice cold 50 mM Tris-HCl, pH 7.4. The amount of [$^3$H]Rauwolscine trapped on the filters was determined by liquid scintillation spectrometry. Nonspecific binding was defined by 1-naphthylpiperazine, 10 $\mu$M. The actual free radioligand concentration was determined by sampling the supernatant of identical tubes in which the bound radioligand was separated from the free radioligand by centrifugation. For competition experiments the final concentration of [$^3$H]Rauwolscine was 2 nM.

Statistical Analysis:

The $K_d$ and $B_{max}$ values from the saturation assays were determined for best fit to a one-site or a two-site binding model using a partial F-test. De Lean, A., A. A. Hancock, and R. J. Lefkowitz, *Mol. Pharmacol.* 21: 5–16 (1981). The following equation was used for a one-site binding model, $$\text{Bound} = \frac{B_{max} \times [L]}{K_d + [L]}$$

where Bound=amount of [$^3$H]5-HT specifically bound, $B_{max}$=maximum number of binding sites, $K_d$=equilibrium dissociation constant and [L]=free concentration of [$^3$H]5-HT, or a two-site binding model, $$\text{Bound} = \frac{B_{max1} \times [L]}{K_{d1} + [L]} + \frac{B_{max2} \times [L]}{K_{d2} + [L]}$$

where Bound=amount of [$^3$H]5-HT specifically bound, $B_{max1}$=maximum number of high affinity binding sites, $B_{max2}$=maximum number of low affinity binding sites, $K_{d1}$=equilibrium dissociation constant for the high affinity site, $K_{d2}$=equilibrium dissociation constant for the low affinity site and [L]=free concentration of [$^3$H]5-HT. The $IC_{50}$ values from the competition assays, the binding parameters for the $IP_3$ standard curve and the $EC_{50}$ and $E_{max}$ values from the $IP_3$ assays were determined by nonlinear regression analysis of four parameter logistic equations (Systat, Systat Inc, Evanston, Ill.). De Lean, A., A. A. Hancock, and R. J. Lefkowitz, *Mol. Pharmacol.*, 21: 5–16 (1981). The $IC_{50}$ values were converted to $K_i$ values using the Cheng-Prusoff equation. Cheng, Y., and W. H. Prusoff, *Biochem. Pharmacol.*, 22: 3099–3108 (1973).

For example, the following cell assays use Human Cells

| Compound | $5HT_{2B}$Cells | $5HT_{2A}$cells | $5HT_{2C}$Cells |
|---|---|---|---|
| Example 1 | 5.97 | 1892.68 | 914.17 |

III. Assay Methods 5-HT$_{2B}$ in vitro:

Male Wistar rats (150–375 g; Laboratory Supply, Indianapolis, Ind.) were sacrificed by cervical dislocation, and longitudinal section of the stomach fundus were prepared for in vitro examination. Four preparations were obtained from one rat fundus. Ring preparations of the extracted jugular vein were prepared as described by Hooker; *Blood Vessels* 14:1 (1977) and Cohen, M. L. *J. Pharamcol. Exp. Ther.* 227:327 (1983). Tissues were mounted in organ baths containing 10 mL of modified Krebs solution of the following composition (millimolar concentrations): NaCl, 118.2; KCl, 4.6; $CaCl_2 \cdot H_2O$, 1.6; $KH_2PO_4$, 1.2; $MgSO_4$, 1.2; dextrose, 10.0; and $NaHCO_3$, 24.8. Tissue bath solutions were maintained at 37° C. and equilibrated with 95% $O_2$ and 5% $CO_2$. Tissues were placed under optimum resting force (4 g) and were allowed to equilibrate for approximately 1 hour before exposure to the test compound. Isometric contractions were recorded as changes in grams of force on a Beckman Dynograph with Statham UC-3 transducers.

Determination of Apparent Antagonist Dissociation Constant:

Noncumulative contractile concentration-response curves for serotonin in the fundus and cumulative concentration response curves in the jugular vein were obtained by a stepwise increase in concentration after washing out the preceding concentrations every 15–20 minutes. Each agonist concentration remained in contact with the tissue for approximately 2 minutes and maximum response to each compound concentration was measured. $ED_{50}$ values were taken as the concentration of agonist that produced half-maximal contraction. After control responses were obtained, tissues were incubated with an appropriate concentration of buffer or antagonist for 1 hour. Responses to serotonin were then repeated in the presence of an antagonist. Concentration responses utilized only one agonist and one antagonist concentration per tissue. In general, successive agonist responses in the presence of buffer treatment were unaltered (average dose ratio was 1.28+/−0.21).

Apparent antagonist dissociation constants ($K_B$) were determined for each concentration of antagonist according to the following equation:

$$K_B = [B]/(\text{dose ratio} - 1)$$

where [B] is the concentration of the antagonist and dose ratio is the $ED_{50}$ of the agonist in the presence of the antagonist divided by the control $ED_{50}$. Generally, parallel shifts in the concentration-response curves occurred in the presence of antagonists. The results were expressed as the negative logarithm of the KB (i.e., −log $K_B$). Calculations were completed using known methods. Zaborowsky, B. R. *J. Pharmacol. Methods* 4:4165 (1980).

Compounds of this invention were tested and demonstrated 5-HT$_{2B}$ receptor activity using this described in vitro method.

In vivo Studies:

Sprague-Dawley Rats (250–300 g) were fasted overnight. The rats were anesthetized with urethane (250 mg) delivered intraperitoneally. The abdominal cavity was opened and strain guage transducers were sewn on the antimesenteric border of the colon. The transducers were oriented to record circular muscle contractions. The animal body temperature was maintained by a heating pad. An intravenous catheter was inserted into the jugular vein for drug administration. The carotid blood pressure was also monitored. Output of the strain guage transducers was graphed on a Beckman Dynograph. Baseline motility was monitored for 30 minutes. At the end of the 30 minute period, a vehicle control dose was administered and motility was recorded for an additional 15 minutes. A serotonin dose response was developed. Successively higher doses of serotonin were administered at 15 minute intervals. An $ED_{50}$ dose was calculated, which was the dose producing half maximal contraction. In antagonist experiments, historical $ED_{50}$ dose was administered to validate the experimental set up. Next, a dose of antagonist was given. The motility was monitored for 15 minutes. After the 15 minute monitoring, an $ED_{50}$ dose was administered. Motility was evaluated by measuring the number of contractions and multiplying them by the amplitude of contractions over a set time period to provide a Motility Index. The percent inhibition was calculated from the vehicle (no antagonist) treated group. A minimum of three rats were used for each concentration and data from different animals was pooled to determine $ED_{50}$ values.

Compounds exhibiting activity at the 5HT$_{2B}$ receptor are useful for treating disorders related to the modulation of the 5HT$_{2B}$ receptor. For example, compounds having 5HT$_{2B}$ antagonist activity reduce the spasticity of the colon. Thus, these compounds are useful for the treatment of functional bowel disorders including irritable bowel syndrome and irritable bowel syndrome-related symptoms. The antispasmodic effect of such compounds can reduce abdominal pain associated with functional bowel disorders. Additionally, the $5HT_{2B}$ receptor is localized in other organs such as the brain, bladder, blood vessels, stomach, and uterus, indicating that additional conditions are $5HT_{2B}$ mediated.

While it is possible to administer a compound of the invention directly without any formulation, the compounds are preferably employed in the form of a pharmaceutical formulation comprising a pharmaceutically acceptable excipient and at least one compound of the invention. Such compositions contain from about 0.1 percent by weight to about 90.0 percent by weight of a present compound. As such, the present invention also provides pharmaceutical formulations comprising a compound of the invention and a pharmaceutically acceptable excipient therefor.

In making the compositions of the present invention, the active ingredient is usually mixed with an excipient which can be a carrier, or a diluent or be diluted by a carrier, or enclosed within a carrier which can be in the form of a capsule, sachet, paper or other container. When the carrier serves as a diluent, it can be a solid, semi-solid, or liquid material which acts as a vehicle, excipient, or medium for the active ingredient. Thus, the composition can be in the form of tablets, pills, powders, lozenges, sachets, cachets, elixirs, emulsions, solutions, syrups, suspensions, aerosols (as a solid or in a liquid medium), and soft and hard gelatin capsules.

The compounds of the invention may be delivered transdermally, if desired. Transdermal permeation enhancers and delivery systems, including patches and the like, are well known to the skilled artisan.

Examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxy- benzoates, talc, magnesium stearate, water, and mineral oil. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

The compounds of this invention may be delivered transdermally using known transdermal delivery systems and excipients. Most preferably, a compound of this invention is admixed with permeation enhancers including, but not limited to, propylene glycol, polyethylene glycol monolaurate, and azacycloalkan-2-ones, and incorporated into a patch or similar delivery system. Additional excipients including gelling agents, emulsifiers, and buffers may be added to the transdermal formulation as desired.

For oral administration, a compound of this invention ideally can be admixed with carriers and diluents and molded into tablets or enclosed in gelatin capsules.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect in association with a suitable pharmaceutical carrier.

In order to more fully illustrate the operation of this invention, the following formulation examples are provided. The examples are illustrative only, and are not intended to limit the scope of the invention. The formulations may employ as active compounds any of the compounds of the present invention.

Formulation 1

Hard gelatin capsules are prepared using the following ingredients:

|  | Amount Per Capsule | Concentration by Weight (percent) |
| --- | --- | --- |
| spiro-9,9[2-(3,5-dimethoxy)-1,2,3,4-tetrahydronaphthyl]-5-methyl-1,2,3,9-tetrahydro-8H-pyrido indole hydrochloride | 250 mg | 55.0 |
| starch dried | 200 mg | 43.0 |
| magnesium stearate | 10 mg | 2.0 |
|  | 460 mg | 100.0 |

The above ingredients are mixed and filled into hard gelatin capsules in 460 mg quantities.

Formulation 2

Capsules each containing 20 mg of medicament are made as follows:

|  | Amount Per Capsule | Concentration by Weight (percent) |
| --- | --- | --- |
| spiro-9,9[2-(3,4-dimethoxy)-1,2,3,4-tetrahydronaphthyl]-5-methyl-1,2,3,9-tetrahydro-8H-pyrido indole hydrochloride | 20 mg | 10.0 |
| starch | 89 mg | 44.5 |
| microcrystalline cellulose | 89 mg | 44.5 |
| magnesium stearate | 2 mg | 1.0 |
|  | 200 mg | 100.0 |

The active ingredient, cellulose, starch, and magnesium stearate are blended, passed through a No. 45 mesh U.S. sieve and filled into a hard gelatin capsule.

Formulation 3

Capsules each containing 100 mg of medicament are made as follows:

|  | Amount Per Capsule | Concentration by Weight (percent) |
| --- | --- | --- |
| spiro-9,9[2-(3-methoxy 4-chloro)-1,2,3,4-tetrahydronaphthyl]-5-ethyl-1,2,3,9-tetrahydro-8H-pyrido indole hydrochloride | 100 mg | 30.00 |
| polyoxyethylene sorbitan monooleate | 50 mg | 0.02 |
| starch powder | 250 mg | 69.98 |
|  | 350 mg | 100.00 |

The above ingredients are thoroughly mixed and placed in an empty gelatin capsule.

Formulation 4

Tablets containing 10 mg of active ingredient are made as follows:

| | Amount Per Tablet | Concentration by Weight (percent) |
|---|---|---|
| spiro-9,9[2-(3,4-dichloro)-1,2,3,4-tetrahydronaphthyl]-5-methoxy-1,2,3,9-tetrahydro-8H-pyrido indole tartrate | 10 mg | 10.0 |
| starch | 45 mg | 45.0 |
| microcrystalline cellulose | 35 mg | 35.0 |
| polyvinylpyrrolidone (as 10% solution in water) | 4 mg | 4.0 |
| sodium carboxymethyl starch | 4.5 mg | 4.5 |
| magnesium stearate | 0.5 mg | 0.5 |
| talc | 1 mg | 1.0 |
| | 100 mg | 100.0 |

The active ingredient, starch and cellulose are passed through a No. 45 mesh U.S. sieve and mixed thoroughly. The solution of polyvinylpyrrolidone is mixed wiht the resultant powders which are then passed through a No. 14 mesh U.S. sieve. The granule so produced is dried at 50°–60° C. and passed through a No. 18 mesh U.S. sieve. The sodium carboxymethyl starch, magnesium stearate and talc, previously passed through a No. 60 mesh U.S. sieve, are then added to the granule which, after mixing, is compressed on a tablet machine to yield a tablet weighing 100 mg.

We claim:

1. A compound of formula I

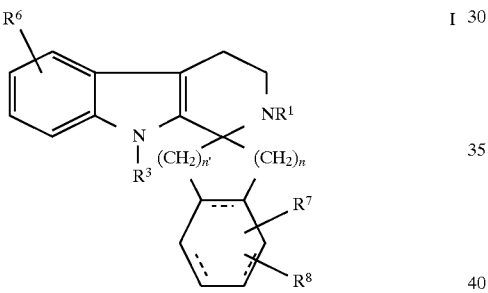

wherein $R^1$ and $R^3$, independently, are hydrogen or $C_1$–$C_3$ alkyl;

$R^6$ is hydrogen, $C_1$–$C_6$ alkyl, $C_2$–$C_6$ alkenyl, halo, halo($C_1$–$C_6$)alkyl, halo($C_2$–$C_6$)alkenyl, $COR_5$, $C_1$–$C_{10}$ alkanoyl, $CO_2R_5'$, ($C_1$–$C_6$ alkyl)$_m$ amino, $NO_2$, —$SR_5$, or $OR_5$;

$R^7$ and $R^8$, independently, are an $R^6$ group or $C_7$–$C_{16}$ arylalkyl;

n and n', independently, are 1, 2, or 3;

m is 1 or 2;

$R_5$ is hydrogen or $C_1$–$C_4$ alkyl;

$R_5'$ is $C_1$–$C_4$ alkyl; and

--- is optionally a bond; or a pharmaceutically acceptable salt or solvate thereof.

2. A compound of claim 1 wherein $R^1$ is hydrogen.

3. A compound of claim 2 wherein $R^3$ is hydrogen.

4. A compound of claim 3 wherein --- are double bonds to provide an aromatic ring.

5. A compound of claim 4 wherein n is 1 and n' is 1.

6. A compound of claim 4 wherein n is 2 and n' is 1.

7. A compound of claim 4 wherein n is 2 and n' is 2.

8. A compound of claim 3 wherein $R^6$ is located at the 5 position.

9. A compound of claim 8 wherein $R^6$ is methyl, chloro or bromo.

10. A compound of claim 9 wherein $R^7$ and $R^8$ are independently methoxy or ethoxy.

11. A compound of claim 1 wherein $R^7$ and $R^8$ are at the 3 and 4 positions of the phenyl ring.

12. A compound of claim 1 wherein $R^7$ and $R^8$ are methoxy or ethoxy.

13. A compound of claim 1 wherein the compound is selected from the group consisting of

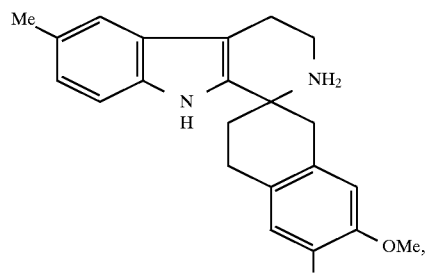

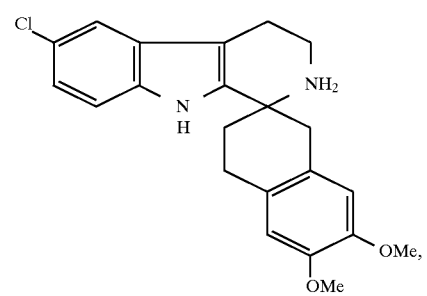

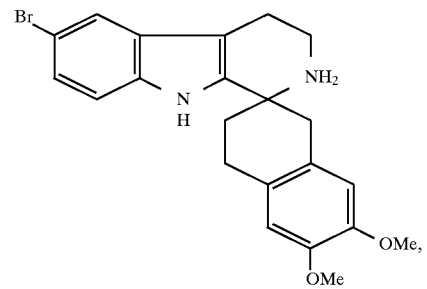

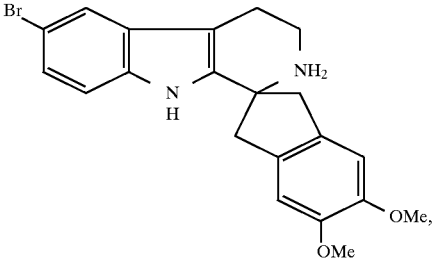

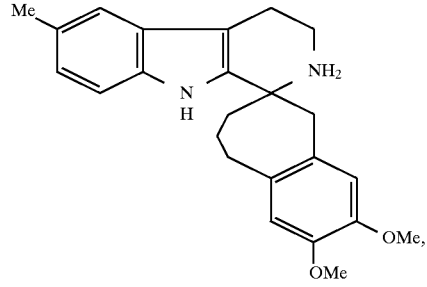

and

-continued

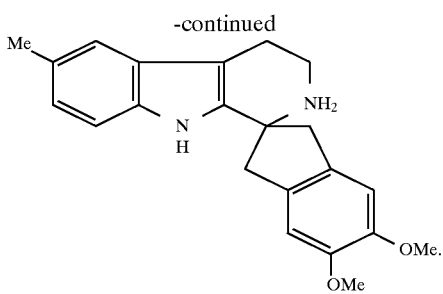

14. A pharmaceutical formulation comprising a compound of claim 1 and one or more pharmaceutically acceptable excipients therefor.

15. A method for treating a mammal suffering from or susceptible to a condition associated with $5HT_{2B}$ modulation, which comprises administering to said mammal an effective amount of a compound of claim 1.

16. A method of claim 15 for treating a mammal suffering from, or susceptible to a Functional Bowel Disorder.

17. A compound of claim 4 wherein n is 1 and n' is 2.

18. A method for treating a human suffering from, or susceptible to, a condition associated with $5HT_{2B}$ modulation, which comprises administering an effective amount of a compound of claim 1 to the human.

19. A method of claim 18 wherein the condition is a Functional Bowel Disorder.

20. A method of claim 18 wherein the condition is migraine.

21. A method of claim 18 wherein the condition is a cardiovascular condition.

22. A method of claim 18 wherein the condition is hypertension.

23. A method of claim 18 wherein the condition is a vascular occlusive disease.

* * * * *